United States Patent [19]
Cunningham et al.

[11] Patent Number: 5,737,872
[45] Date of Patent: Apr. 14, 1998

[54] FORMULATION FOR SYNTHETIC SEED

[75] Inventors: James E. Cunningham; Danielle Julie Carrier; David I. Dunstan, all of Saskatoon, Canada

[73] Assignee: National Research Council of Canada, Ottawa, Canada

[21] Appl. No.: 692,949

[22] Filed: Aug. 7, 1996

[51] Int. Cl.⁶ .............................. A01C 1/06; A01C 21/00; A01C 1/00; A01B 79/00
[52] U.S. Cl. .................................... 47/57.6; 47/58
[58] Field of Search .................................. 47/57.6, 58

[56] References Cited

U.S. PATENT DOCUMENTS

| | | | |
|---|---|---|---|
| 4,777,762 | 10/1988 | Redenbaugh et al. | 47/57.6 |
| 5,093,130 | 3/1992 | Fujii et al. | 424/463 |

FOREIGN PATENT DOCUMENTS

| | | | |
|---|---|---|---|
| 9207457 | 3/1992 | European Pat. Off. | A01C 1/06 |

*Primary Examiner*—David T. Fox
*Assistant Examiner*—Kent L. Bell
*Attorney, Agent, or Firm*—J. Wayne Anderson

[57] ABSTRACT

The invention disclosed is a synthetic seed and a method for the manufacture thereof. The seed comprises a plant propagule which is capable of producing an entire plant, encapsulated in a material including an inert filler, a binder and water. The synthetic seed has a prescribed selected water-activity to maintain viability until exposed to germination permissive conditions, and is of sufficient mechanical strength/hardness for use with mechanical seeding devices.

11 Claims, 9 Drawing Sheets ic  # 5,737,872

FORMULATION FOR SYNTHETIC SEED

BACKGROUND OF THE INVENTION

This invention relates generally to plant reproduction, and in particular to a synthetic seed and a method for the manufacture thereof.

1. Field of the Invention

Synthetic seeds generally include a plant propagule, embedded in various supporting materials.

A plant propagule is understood herein to be any plant tissue which is capable of developing into a complete plant when subject to suitable conditions, including somatic embryos, zygotic embryos, germ-line tissue and the like.

2. Description of the Prior Art

A good general review of the prior art is found in Synseeds: Applications of Synthetic Seeds to Crop Improvement, Ed. Redenbaugh M. Keith, 1992, CRC Press Inc., Boca Raton Fla., USA.

A specific example of a synthetic seed is disclosed in Physico-Chemical Properties of the Encapsulation Matrix and Germination of Carrot Somatic Embryos, Timbert, Raphaelle et al., Biotechnology and Bioengineering, Vol. 46, Pp 573-578 (1995). This reference discloses carrot somatic embryos encapsulated in alginate gel beads, and including small amounts( e.g. 0.6%) of mineral additives (kaolin and silica are mentioned) to increase resistance to rupture and depress germination.

In U.S. Pat. No. 4,777,762 which issued on 18 Oct. 1988 in the name of M. Keith Redenbaugh et al., another synthetic seed is disclosed which comprises a meristematic plant tissue encapsulated in a hydrated gel, wherein the tissue is dehydrated to a water content of below 99.9%, by removing a portion of the water so that the plant tissue is no longer saturated with water. Dehydration is effected either before or after encapsulation of the tissue in the gel.

It is noted that no means is disclosed for controlling the extent of dehydration.

SUMMARY OF THE INVENTION

It is an object of the invention to provide a synthetic seed which may be stored for long periods of time without germinating, while maintaining vigour so that the seed will germinate upon exposure to germination permissive conditions.

It is another object of the invention to provide a synthetic seed which is capable of withstanding the rigors of mechanical sowing devices.

According to one aspect of the invention a synthetic seed is provided, comprising, a plant propagule capable of producing an entire plant, and an encapsulating material including a finely divided substantially biologically and chemically inert filler, a binder and water, the synthetic seed having a prescribed/selected water activity, such that propagule viability is maintained and germination will occur when exposed to germination permissive conditions, and to provide sufficient mechanical strength/hardness for use with mechanical seeding devices.

According to another aspect of the invention, a method is provided for the manufacture of a synthetic seed, comprising:

(a) providing a plant propagule which is capable of producing an entire plant, (b) encapsulating the plant propagule in a material including a finely divided substantially biologically and chemically inert filler, a binder and water, and (c) adjusting the water content to provide a prescribed/ selected water activity for the synthetic seed, such that propagule viability is maintained and germination will occur when exposed to germination permissive conditions, and to provide sufficient mechanical strength/hardness for use with mechanical seeding devices.

DESCRIPTION OF THE PREFERRED EMBODIMENTS

Figure 1:
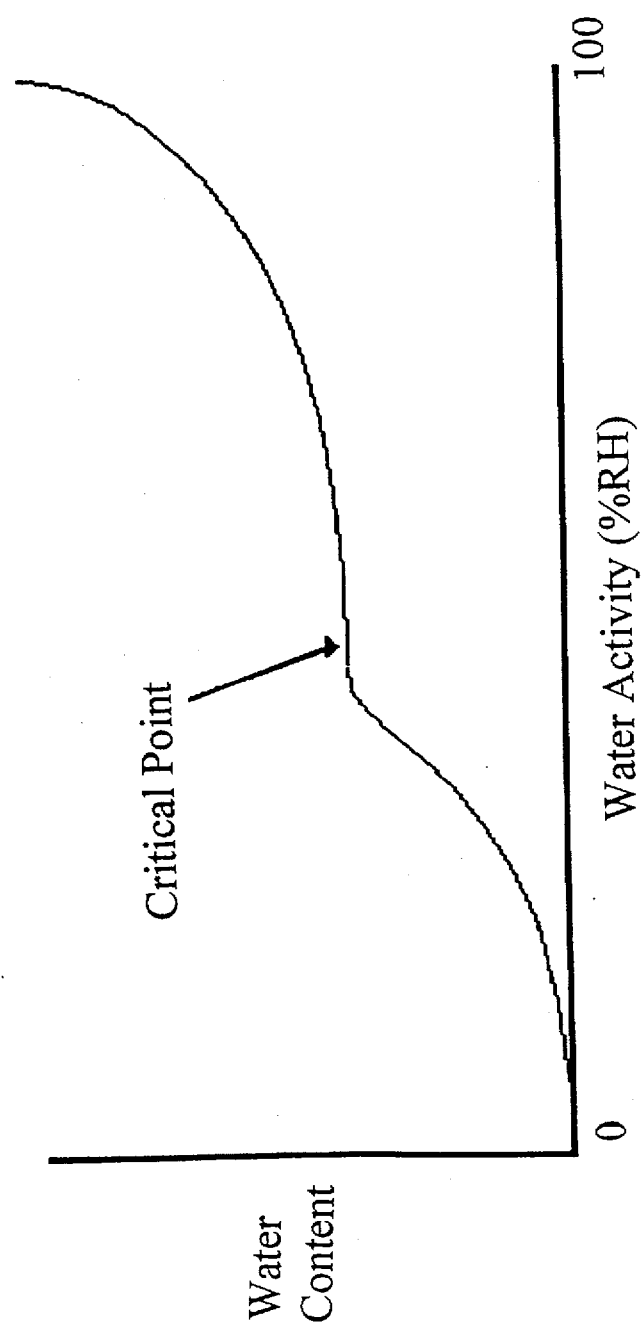
FIG. 1 is a moisture sorption isotherm which illustrates the relationship between water content and water activity of a material.

For the purposes of this application, the following definitions have been used:

Filler:

A finely divided material, biologically and chemically inert towards materials it is in contact with, including clays, minerals, and some botanical materials, e.g. silica, kaolin and cellulose.

Binder:

A material or condition causing the adhesion of filler particles to one another and to plant tissue surfaces. Examples include polymers with or without cross-linking agents, ionic solutes, temperature, pH. Specific materials include hydrated gels, e.g. sodium alginate, and other similar materials such as those described in U.S. Pat. No. 4,777,762, the disclosure of which is incorporated herein by reference.

Dispersion:

An aqueous dispersion of the filler (e.g. silica) and binder (e.g. sodium alginate).

Matrix:

A 3-D structure composed of filler ±binder and ±water. Example: beads formed by dripping the Dispersion into an aqueous solution of a divalent cation (e.g. calcium) complexing agent.

Water Activity:

The partial pressure of water in the vapor phase of a system, relative to the partial pressure of the vapor phase associated with pure water. Commonly expressed in percentage (% relative humidity).

Dessicant:

A material which adsorbs or absorbs water. Also called a sorptive agent or a drying agent.

Delivery:

The process used to transfer synthetic seed from a storage container to a planting medium.

Silica:

Synonyms are "natural silica", and "silicic anhydride".

Chemical composition (elemental) is $SiO_2$.

Mineral structure is "microcrystalline".

Occurs in nature as quartz (as an example).

The form used in our work is finely ground (particle size 1–5 micron).

Silica Gel:

Synonyms are "silicic acid", "precipitated silica".

Chemical composition (elemental) is approximately $H_2SiO_3$.

Occurs in nature as Opal.

The form used in our work is 230–400 mesh (particle size greater than 200 micron).

The epithet "gel" is misleading in the present context because the material is essentially insoluble.

Fumed Silica:

Extremely small particles of $SiO_2$ (approximately 0.007 to 0.014 micron diameter).

Physical properties (colloidal, sorptive) are distinct from Silica due to small particle size and consequently large surface area.

DIFFERENCES BETWEEN OUR INFORMATION AND THE DISCLOSURES OF TIMBERT ET AL. 1995 AND REDENBAUGH U.S. Pat. No. 4,777,762.

Inclusion of Silica:

The inclusion of silica in a gel matrix, as disclosed in the aforementioned Timbert et al. 1995, is for a different purpose and used in a radically different proportion than in our work. Timbert et al. included small amounts of silica as a means of altering the gel strength and water potential of the bead. We included large amounts of silica as a filler to provide mass when the bead is dried. Timbert et al. (1995) added 0.6% silica to a 1% alginate sol (i.e., 0.01 part alginate, 0.006 parts silica, 0.984 parts water). For example, we use an aqueous dispersion including silica in the range of 30% (i.e., 0.01 parts alginate, 0.3 parts silica, 0.69 parts water. If beads of equivalent volume were prepared and dried, our bead would have about 19.4 times the mass of the Timbert et al. formulation.

Water Activity:

The relationship between water content and water activity is a fundamental principle, usually presented in the form of a moisture sorption isotherm or moisture desorption isotherm. We make use of this principle in our work, to determine the amount of drying agent required to adjust the water activity of the synthetic seed.

Water Content:

The patent of Redenbaugh (U.S. Pat. No. 4,777,762) describes a propagule encapsulated in a gel and dried below 99.9% of saturation. No filler is present. The saturation level is presumably the maximum water holding capacity of the gel. This would include all levels of hydration from wet gel to dry solid. According to the present invention, the level of hydration is adjusted to result in a predetermined water activity, which is within the range that is compatible with the propagule ie. a range of 0 to 99% relative humidity. The water activity range may be specific to each propagule type or source. In addition, in our work the level of hydration and bead formulation specifically results in a bead that is spherical or subspherical (therefore has handling properties similar to natural seed), is hard, and has the feel and appearance of being "dry" in the common sense of the word.

Water Absorbing Compounds:

The patent of Redenbaugh (U.S. Pat. No. 4,777,762) lists "water absorbing compounds" as one of many adjuvants. The adjuvants are described as constituents of the synthetic seed. No mention is made of the use of external water absorbing solids to adjust the water activity of a synthetic seed. In our work, encapsulated plant propagules are exposed to, and then removed from, a water absorbing compound (silica gel is used as an example). Our work refines this prior art by providing a means for controlling the rate of water removal and the final water activity. The inclusion of silica in our bead is not for water absorbing purposes (the water sorption property of silica is negligible).

ADVANTAGES OF THE DIFFERENCES

Water Activity:

This is a fundamental distinction between our work and prior disclosures. Our process comprises a means to determine the water activity required by the propagule, a means for providing the required water activity in the artificial seed, and a means for controlling the rate at which the water activity is adjusted. The advantages are that the water activity is optimized for storage stability of the synthetic seed, and the procedure can be adapted to the specific propagule. We are not aware of any disclosures in which the water activity of the propagule (established by demonstrating equilibrium with its environment or by direct measurement) has been related to storage stability. We are not aware of any disclosures in which the optimal water activity is related to the water content of an encapsulating material.

Inclusion of Silica:

The inclusion of silica, or other suitable fillers described herein, provides a bead of adequate size, shape, and mass for the required handling characteristics. Silica was selected as one example of a filler having negligible water absorbing property: that is, at high water activity, the matrix bead has low water content. We are not aware of disclosures in which fillers have been used as a means to retain size, shape and mass in a formulation that is also designed to retain the necessary water activity/content for viability of embryos. Most often fillers have not been used and the coated embryos have lacked the desired size, mass, or shape for use as seed substitutes when dehydrated.

Water Content:

The formulation permits dehydration to a water content at which water activity may be high (e.g., 97% RH) but the corresponding water content is low (e.g., ca. 4.5% water [water/dry matter]). The result is a bead which has the handling characteristics of a natural seed (hard and dry feel) but provides a water activity sufficiently high for survival of the propagule, without sufficient free water for germination to occur. We are not aware of disclosures in which the water content of synthetic seed is adjusted by controlled rates or increments to a final water activity which will prevent germination, retain viability, while at the same time produce a hard, seed-like structure (e.g. appropriate size, shape and mass).

FIG. 1 is intended to clarify the preceding text by illustrating water sorption. The amount of water bound to a surface depends on the water activity to which it is equilibrated (% RH being a measure of water activity). When water activity is increased to the extent that the available surface is occupied by water molecules (the critical point), further increases in water activity result in additional water associating with the bound water layer (the additional water being "free" or solvent water). Depending on the distance between surfaces and the contact angle of water with the surface (a function of surface tension and the properties of the material), free water will be held by capillation. The relationship between the mass of water adsorbed, and water activity, is illustrated in FIG. 1. The curve shown is the moisture sorption isotherm. The shape of the curve, the RH at which the critical point occurs, and the specific water content at each humidity, are specific to each material. In the present context, the surfaces represent the surface of silica particles and alginate within a synthetic seed matrix. The synthetic seed matrix is a porous aggregate of silica particles, bound together with a small amount of alginate (for example, 1 part alginate to 30 parts silica) and water. Due to the low water sorption capacity of silica, the synthetic seed matrix only binds an amount of water equal to approximately 4.5% of its own weight, at 97% RH. The fully reconstituted gel (e.g., if the synthetic seed were placed in water and allowed to equilibrate) contains an amount of water that is approximately 220% of the dry weight of the bead.

Unexpected Results.

Properties of the formulation:

The use of the filler resulted in a bead which has a hard, dry feel and appearance at high water activity, due to its low water content at high water activities. There have been many prior attempts to modify alginate gel beads to provide a hard, non-sticking surface, but the existing disclosures do not accomplish this by dehydration to a low water content (see Redenbaugh [ed.], Synseeds Applications of Synthetic Seeds to Crop Improvement, CRC Press, 1993, pp 50–58.). The unexpected result of our formulation is that a hard, dry-feeling synthetic seed with adequate size and shape, which possesses a water activity at or above the minimum required for embryo viability, is obtained. The use of the minimum water activity serves the purpose of preventing germination during storage.

Dehydration:

Prior disclosures consist of procedures which do not readily separate, or control, the characteristics of rate of water removal and final water activity of synthetic seeds. Precise control over the rate of water removal and over the final water activity is achieved with our method. Our method of dehydration can be used to incrementally reduce water potential at desired time intervals over a desired period of time. Direct contact of the hydrated (freshly prepared synthetic seed) with drying agent results in rapid transfer of water, but the mass of water transferred is precisely limited by the mass of drying agent used. Adjustment to a desired water activity by our method can be attained within about 30 minutes.

Rehydration:

The formulation permits rapid transfer of water and nutrients to the embryo, when synthetic seed are placed on a suitable medium. The formulation readily rehydrates, equilibrating with the water activity of the medium, and allows sufficient diffusion of nutrients from the medium to the embryo to permit germination.

Basic procedure for formulating synthetic seeds:

(i) Embryos are placed in an aqueous dispersion of an inert, finely divided material (filler).

(ii) An additional agent(s) or condition is applied (binder) to form an aggregate (matrix) of the filler and binder containing one (or more) embryo. This constitutes the synthetic seed.

(iii) Water is removed from the synthetic seed to a prescribed final water content by exposure of the synthetic seed to a finely divided desiccant. This is added once, or in increments over a period of time, to achieve a prescribed rate of water removal from the embryo.

The final water content of the synthetic seed will correspond to a water activity at which the embryos will be germinable when placed under germination-permissive conditions. This water activity is determined by experiment for each variety of embryo used in the synthetic seed.

This final water content is achieved by using an amount of drying agent determined through a calculation from the moisture sorption property of the desiccant, the moisture desorption property of the matrix and embryo, and the water content of the synthetic seed before drying.

The calculation is as follows:

$$M_d = (1/a)(FW_s - DW_s - bDW_e - c(DW_s - DW_e))$$

where:

$M_d$=The mass of desiccant required $FW_s$=Weight of the synthetic seed that is to be dried, before drying $DW_s$=Dry weight of synthetic seed that is to be dried (estimated by drying a sample of the synthetic seed to a constant weight, at 105° C.

$DW_e$=Dry weight of embryo(s) contained in the synthetic seed that is to be dried.

Estimated from the following:

(i) dry weight of a sample of embryos (ii) number of embryos in the dried sample number of embryos known to be in the synthetic seeds to be dried.

a=Mass (g) of water bound by 1 g of desiccant equilibrated to the final water activity for the synthetic seed. Determined from the moisture sorption isotherm of the desiccant.

b=Mass (g) of water bound by 1 g of embryos at the final water activity for the synthetic seed. Determined from the moisture desorption isotherm of the embryos.

c=Mass (g) of water bound by 1 g of the matrix at the final water activity for the synthetic seed. Determined from the moisture desorption isotherm of the matrix.

The synthetic seed is placed either with or separate from the desiccant, in a water vapor impermeable container to prevent gain or loss of water from the environment.

The synthetic seed is germinated by delivery to a germination medium which supplies the water, nutrient, and temperature requirements of the embryo. These requirements are determined by experiment for each variety of propagule used. It will be appreciated by those skilled in the art that the requirement for nutrients in the germination medium may be replaced by inclusion of nutrients in the synthetic seed.

Experimental development:

CAPSULE MATERIALS

Based on prior information, alginate encapsulation techniques were adopted as the preferred method for forming an artificial seed matrix. A fine powder of amorphous silica was selected to serve as an inert filler, to provide adequate mass for an artificial seed. Proportions of silica (the basic matrix material) and alginate binding agent e.g. alginic acid, sodium salt, medium viscosity, Sigma Chemical Company, cat. no. A-2033 were investigated to obtain a suspension with suitable flow characteristics for bead (synthetic seed) formation by calcium complexation (i.e. by calcium chloride) or other sources of divalent cation, and for appropriate size and mass of the resulting bead. The appropriate concentration of alginate was first determined using graded amounts of alginate in 40% (w/w) suspensions of silica; the effect of silica concentration was then assessed using 1% alginate. The proportions of silica and alginate in each sample are tabulated in Table 1 below, with a description of the resulting bead forming characteristics. Beads were formed by dripping the suspensions from a syringe (standard Luer connector served as aperture for drop formation) from a height of 5 cm into stirring, 50 mM $CaCl_2$.

TABLE 1

| Sample No. | Dispersion Composition (w/w) | | Description | |
|---|---|---|---|---|
| | Alginate | Silica | Dispersion | Beads |
| 1 | 2.00 | 40 | Viscous, poor flowability | Beads with a long "tail" were formed |
| 2 | 1.00 | 40 | Good flowability | Nearly spherical beads with a "tail" |
| 3 | 0.50 | 40 | Low viscosity, flowable | Ellipsoidal to cylindrical beads formed; smooth surface. |
| 4 | 0.25 | 40 | Thin, rapid flowing | Large, irregular (puckered) beads formed |
| 5 | 1.00 | 50 | High viscosity; very poor flowability | Beads with a long "tail" formed. |
| 6 | 1.00 | 40 | Flowable, somewhat viscous | Sub-spheroidal beads with smooth surface |
| 7 | 1.00 | 30 | Good flowability | Uniform, spherical beads with smooth surface |
| 8 | 1.00 | 20 | Good flowability | Slightly sub-spheroidal beads with smooth surface |

The weight and bulk volume of beads (volume occupied by beads in a graduated cylinder) from samples 5 to 8 were recorded before and after drying, as tabulated in Table 2 below.

TABLE 2

| Sample No. | Weight of 100 beads (g) | | Volume of 100 beads (cc) | |
|---|---|---|---|---|
| | wet | dry | wet | dry |
| 5 | 3.9017 | 1.8795 | 4.0 | 2.8 |
| 6 | 5.1580 | 2.4747 | 6.0 | 3.6 |
| 7 | 3.1630 | 1.5834 | 4.0 | 1.8 |
| 8 | 4.1467 | 1.2014 | 6.5 | 1.8 |

The formula for sample 7 beads was selected for further development.

WATER CONTENT-RH RELATIONSHIP

Embryos

Figure 2:
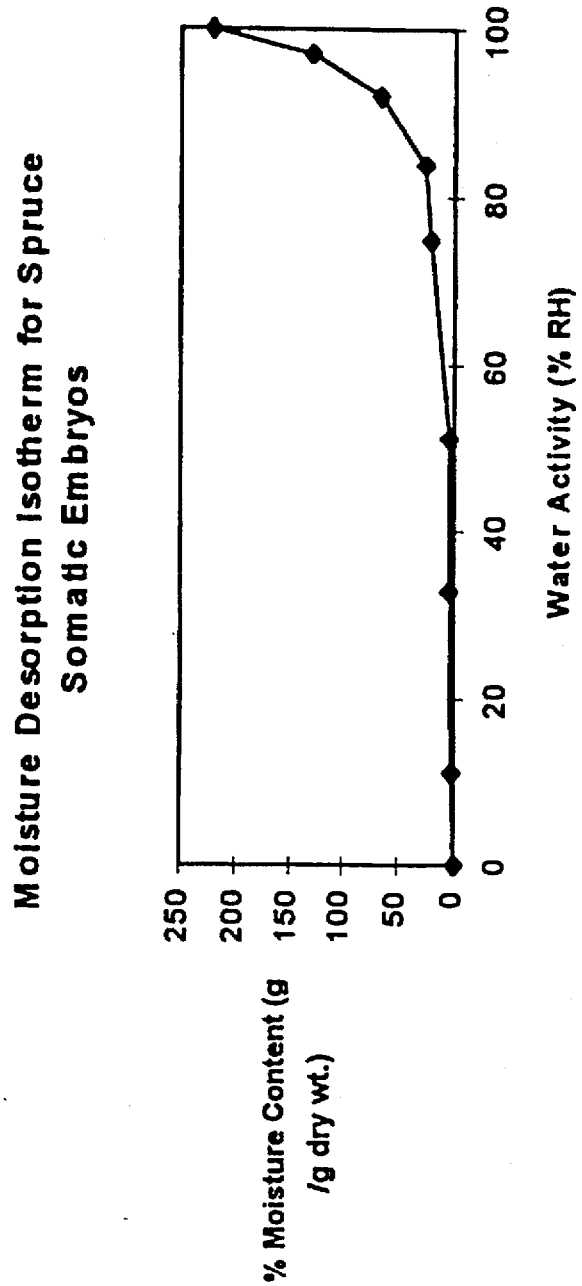
FIG. 2 is also a moisture sorption isotherm, which illustrates the relationship between water content and water activity for spruce somatic embryos.

The relationship between water activity (expressed as relative humidity) and residual embryo water content was determined after allowing fully imbibed embryos to equilibrate to graded relative humidities. Before determining the water activity-water content relationship, the rate of water removal from embryos was determined for the apparatus used, to ensure that equilibrium had been attained. For the apparatus used, the slowest rate of change (corresponding to the highest humidity) attained equilibrium within 250 h; the most rapid rate of change (lowest humidity condition) was at equilibrium within 48 h. This relationship between relative humidity (RH) and water content at equilibrium with each relative humidity is referred to as the moisture desorption isotherm (MDI). The data are presented in FIG. 2.

Figure 3:
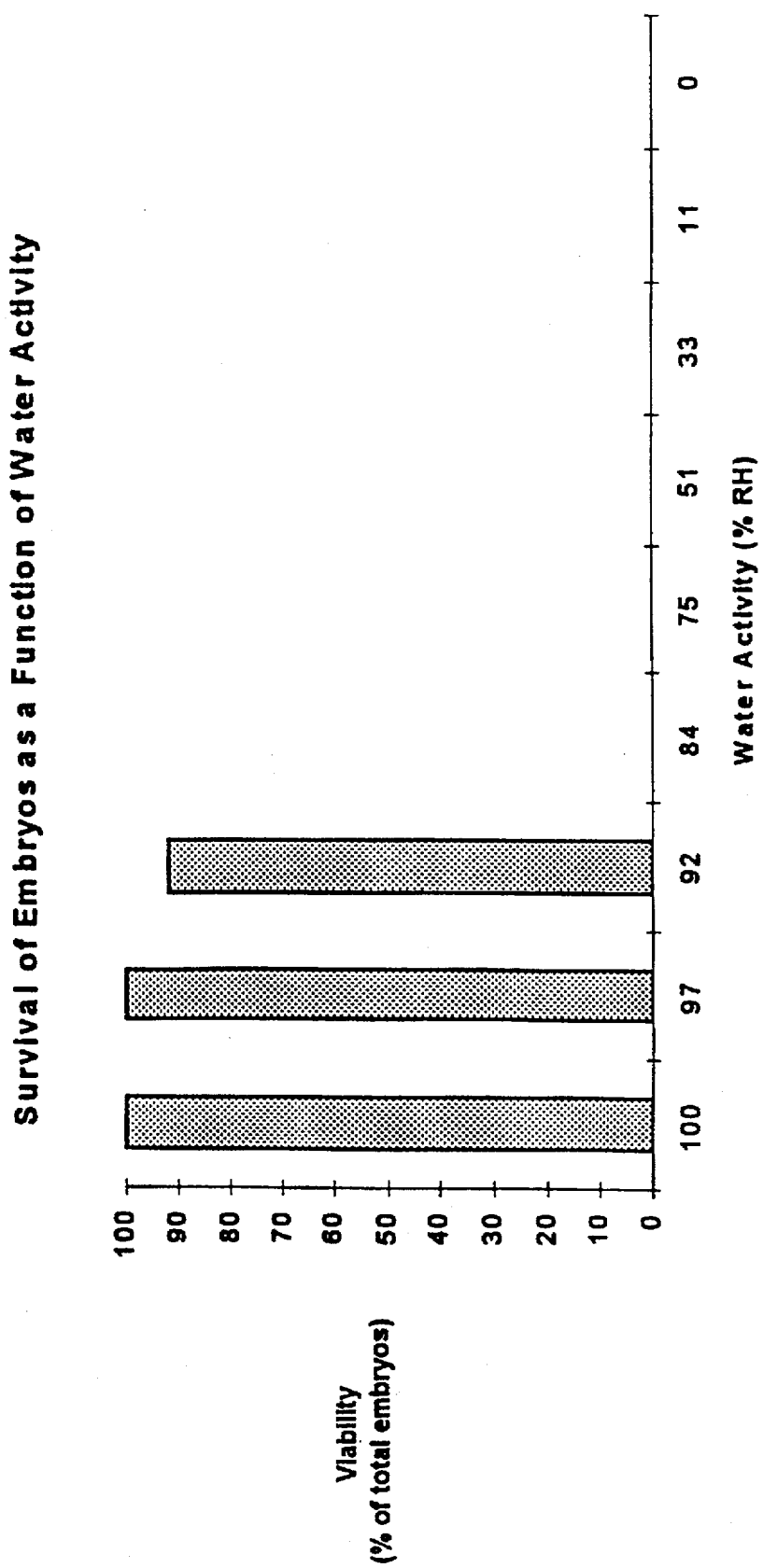
FIG. 3 is a graphical representation of the relationship between water activity and viability of embryos, following storage for thirty days.

The water activity required for retention of embryo viability with storage at 20° C. was determined by storing embryos under graded water activities (as described above) for 30 days. Germinability was assessed by placing the embryos on a standard germination agar medium. Embryos were observed for viability (defined as greening and size increase) after 6 weeks incubation. The results are shown in FIG. 3.

Synthetic Seed Matrix

In order for the synthetic seed matrix to be compatible with the embryos, the matrix must meet the water activity requirements of the embryo. Sufficient dewatering of the matrix to provide acceptable handling characteristics (hardness) for use in nursery seeding equipment is also required. The moisture sorption and desorption of the selected synseed composition (1:30 mass:mass alginate:silica) at 97% RH was therefore recorded.

Figure 4:
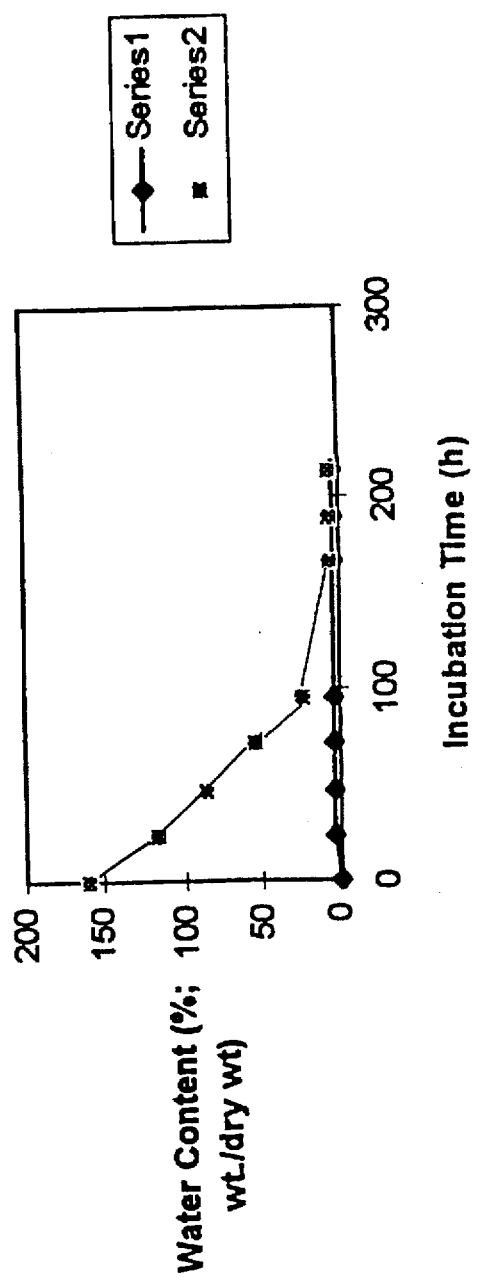
FIG. 4 is a graph which illustrates the relationship between water content and incubation time for a specific seed composition according to the invention.

The results (presented in FIG. 4) indicate that the synthetic seed matrix binds a mass of water equal to about 4.5% of its dry weight, at about 97% RH. The determination was done as described for embryos, above.

Dessicant

Figure 5:
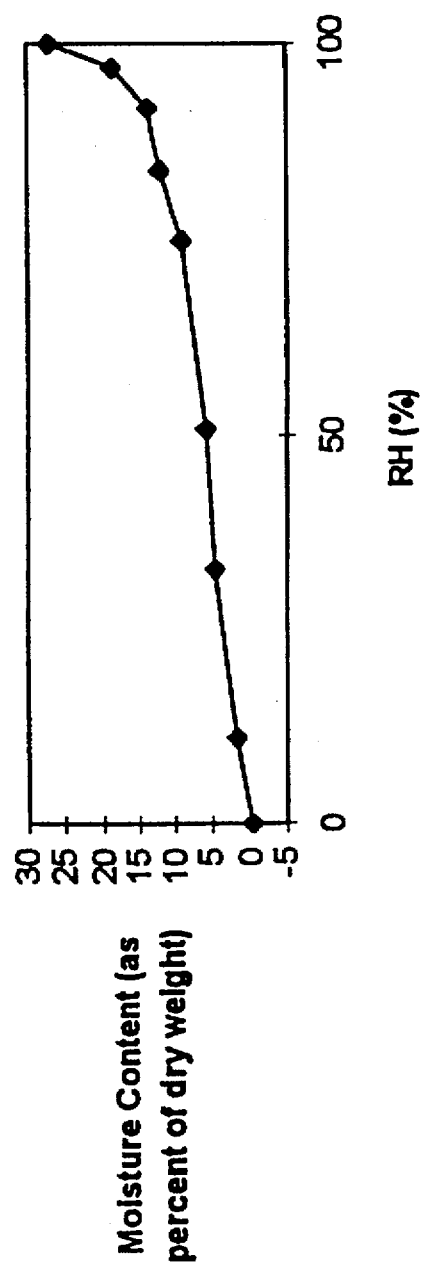
FIG. 5 is a graph which illustrates the drying capability of cellulose.

Dewatering of synthetic seeds was accomplished by exposing the wet beads to a desiccant. The purpose was to develop a scaleable procedure in which the rate and extent of water removal could be controlled. Knowledge of the moisture sorption property of the drying agent is required. Cellulose powder is provided as one example of a suitable desiccant. Other desiccants can be used, for example silica gel. The MSI for the cellulose powder is presented in FIG. 5.

From this data, the amount of cellulose required to dry a known mass of synthetic seed matrix to the water activity desired may be calculated as described above.

WATER ACTIVITY ADJUSTMENT OF SYNTHETIC SEED MATRIX

Figure 6:
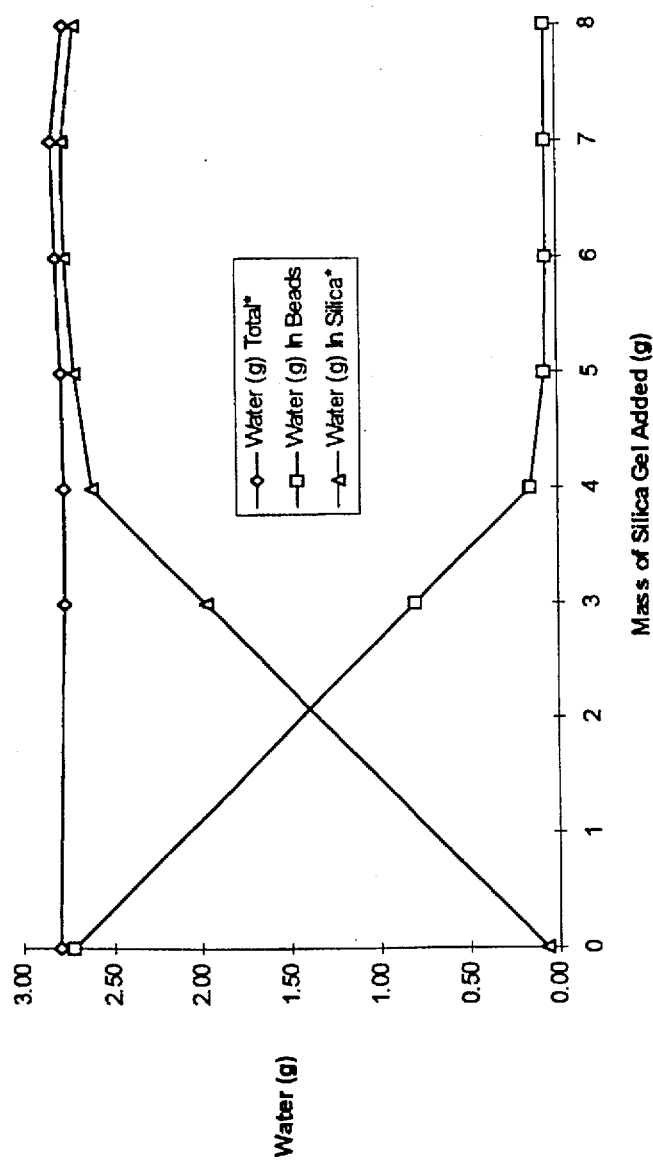
FIG. 6 is a graph which enables determination of the amount of desiccant required to provide the desired water activity over time increments.

The adjustment of synthetic seed matrix water activity was demonstrated by combining silica-alginate beads (prepared as described above) with graded amounts of silica gel as desiccant. The data (shown in FIG. 6) demonstrate how the synthetic seed may be adjusted to the desired water activity, at desired increments over time.

STORAGE STABILITY OF SYNTHETIC SEEDS

Figure 7:
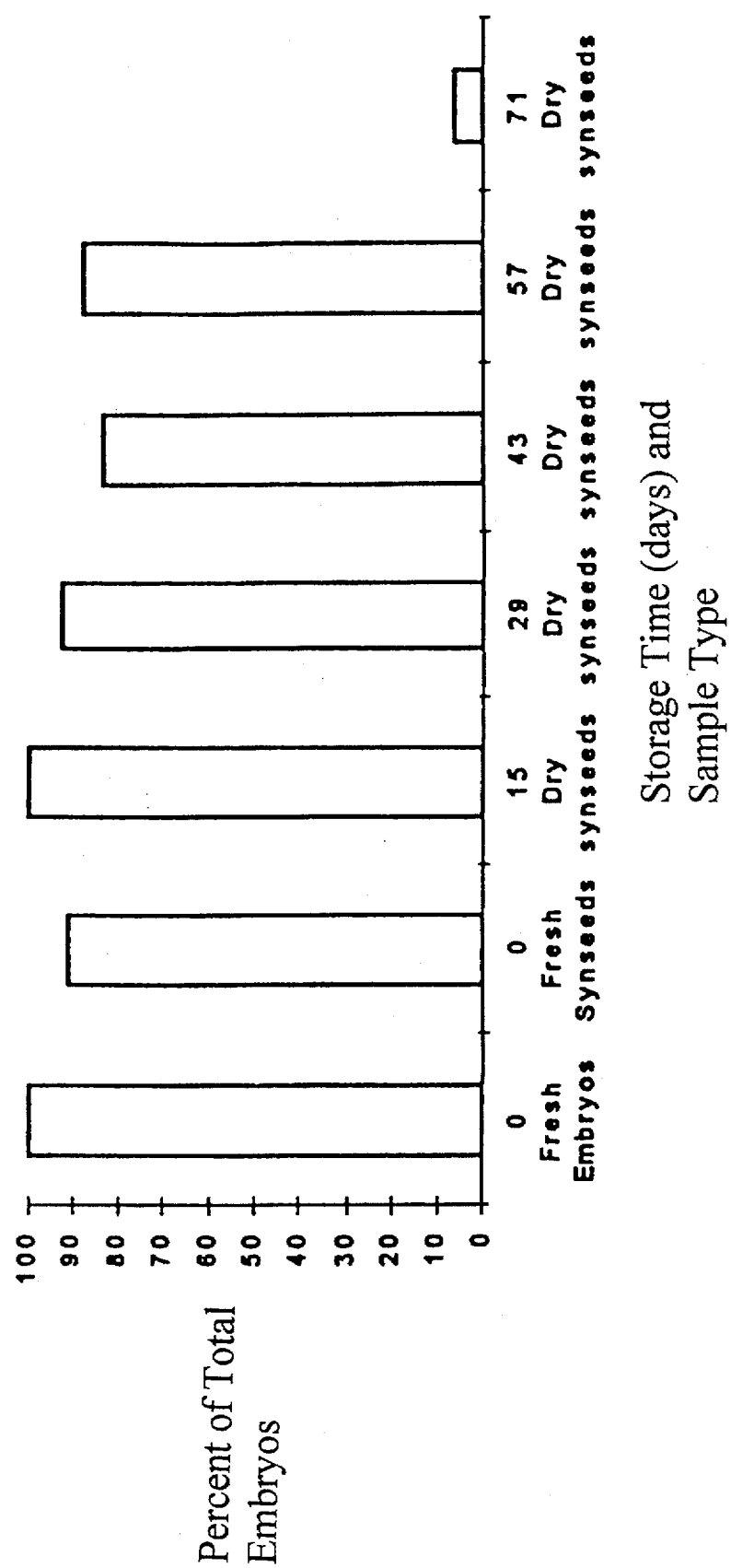
FIGS. 7, 8 and 9 are graphs illustrating the storage stability and maintained viability of synthetic seeds according to the invention.
Figure 8:
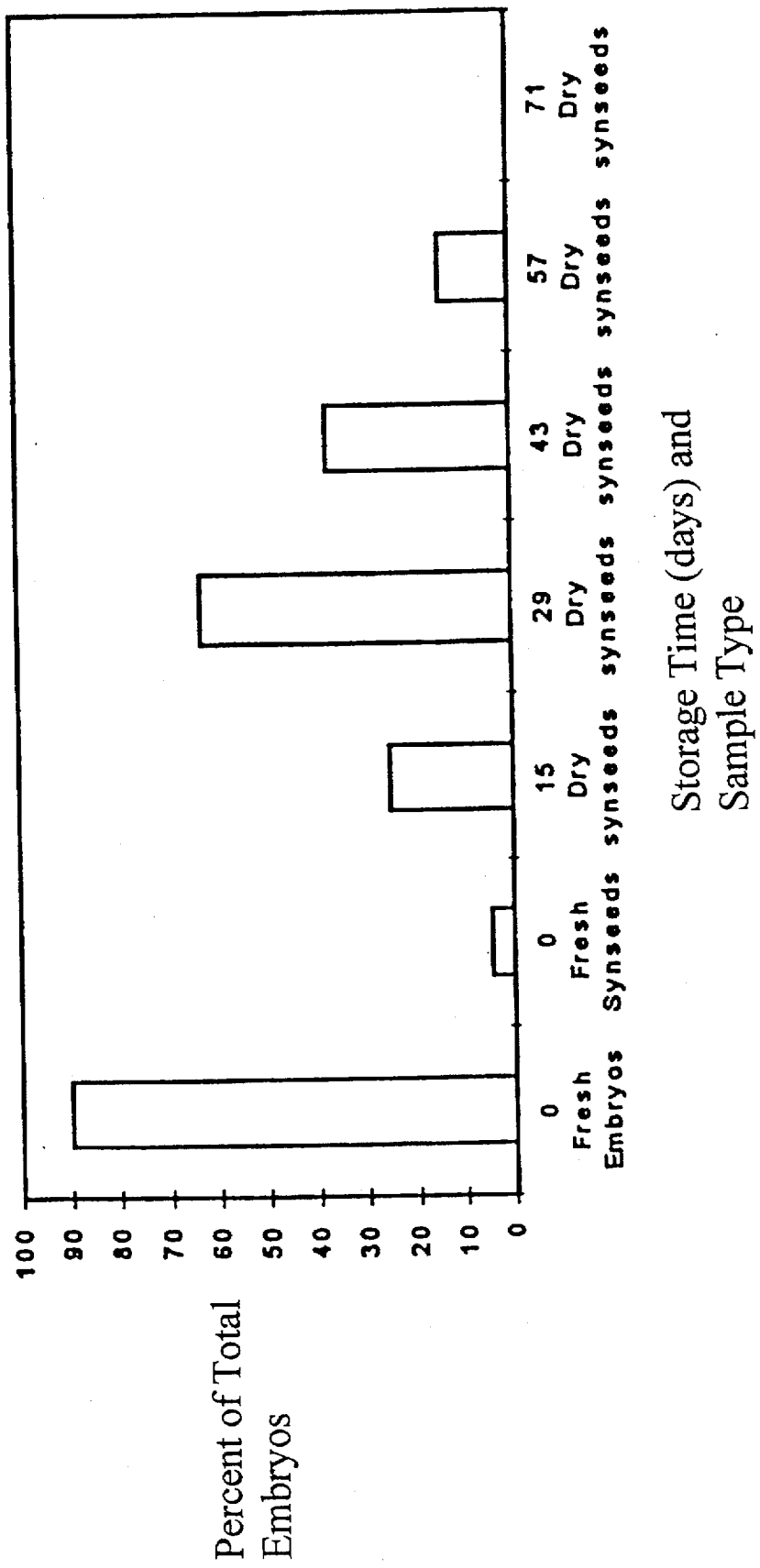
Figure 9:
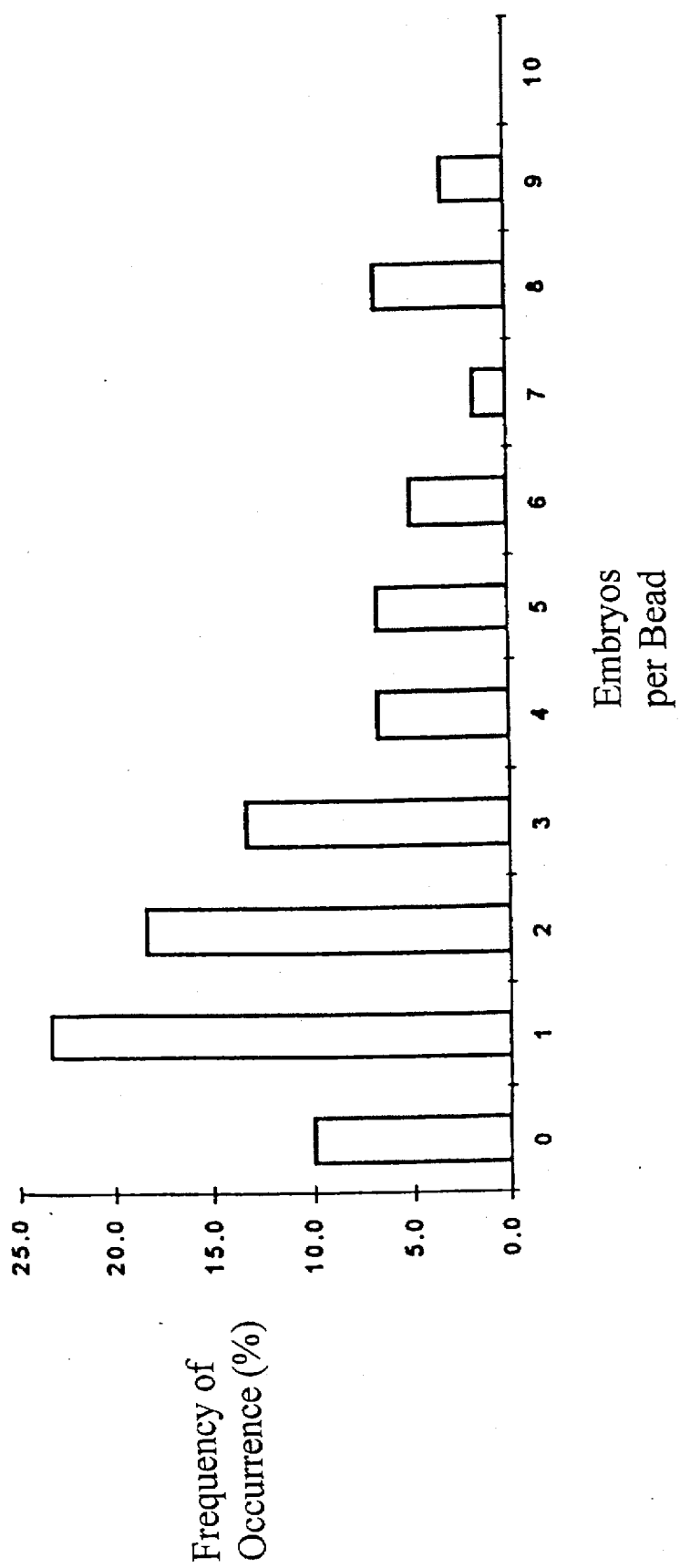

Prototype synthetic seeds were prepared with interior spruce somatic embryos and a matrix composed of silica and alginate (1:30 alginate:silica mass:mass). The water activity of the synthetic seeds was adjusted to approximately 97% RH by contact with silica gel. The synthetic seeds were stored at about 20° C. in sealed containers; samples were tested for geminability at approximately 2 week intervals by placing the synthetic seed on a germination agar medium. The embryos were examined after 6 weeks incubation on the germination medium: the observed characteristics of the synthetic seeds are presented in FIGS. 7, 8 and 9.

The data demonstrate that a high percentage of the encapsulated and dried embryos are viable for at least 52 days under 20° C. storage.

OTHER ADDITIVES

It will be appreciated by those skilled in the art that other adjuvants can be usefully added to the seed composition such as pesticides, herbicides, nutrients, fertilizers. A listing of such adjustments is described in the aforementioned Redenbaugh U.S. Pat. No. 4,777,762, beginning at column 8, line 25, the disclosure of which is incorporated herein by reference.

A FIRST EMBODIMENT OF THE PROCEDURE DEVELOPED THROUGH EXPERIMENTATION:

Materials:

| | |
|---|---|
| Embryos = | Interior spruce stage III somatic embryos. |
| Filler = | Natural silica ($SiO_2$; amorphous, finely ground, particle size 1–5 mm). |
| Binder = | Sodium alginate (medium viscosity: 2% solution = ca. 3500 cp). |
| Dessicant = | Silica gel (precipitated silica; silicic acid; approx. $H_2SiO_3$). 230–400 mesh particle size. |

Processing:

(i) Embryos are removed from maturation condition, and transferred to a sol composed of 1 g sodium alginate, 30 g silica, and 69 g water. Sixty embryos (a range i.e. 20 to 80, can be used) per mL sol are used. This is the Embryo Suspension.

(ii) The Embryo Suspension is passed through a polyethylene tube (ca. 3 mm i.d.) and allowed to fall dropwise into a stirred, 50 mM $CaCl_2$ solution. Each drop results in a synthetic seed.

(iii) Synthetic seeds are separated from the $CaCl_2$ solution, and combined with silica gel to achieve a final water activity of about 97% RH. The mass of silica gel is calculated as outlined in the preceding process description. Approximately 0.75 g anhydrous silica gel per g of synthetic seed is required.

(iv) Dried synthetic seed is separated from the silica gel by sieving, and stored in an air tight (water impermeable) container at 20° C.

(v) Dried synthetic seed may be germinated by placing the seed on a medium (for example, agar-solidified GMD) which supplies the water and nutrient requirements for germination.

A SECOND EMBODIMENT OF THE PROCEDURE DEVELOPED THROUGH EXPERIMENTATION:

Materials:
Propagule=Interior spruce stage III somatic embryos.
Filler=Natural silica ($SiO_2$; amorphous, finely ground, particle size 1–5 mm).
Binder=Sodium alginate (medium viscosity: 2% solution= ca. 3500 cp).
Dessicant=Silica gel (precipitated silica; silicic acid; approx. $H_2SiO_3$). 230–400 mesh particle size.
Other constituents=sucrose, maltodextrin/corn syrup solids $[(C_6H_{10}O_5)_n \cdot H_2O$; product of corn starch hydrolysis; e.g., Maltrin® M040 from Grain Processing Corp., Muscatine, Iowa, 52761, USA].
Processing:

(i) Embryos are removed from maturation condition, washed briefly with water, and transferred to a sol composed of 1.0 g sodium alginate, 30.0 g silica, 1.4 g M040, 0.35 g sucrose, and 67.3 g water. Sixty somatic embryos per mL sol are used. This is the Embryo Suspension.

(ii) The Embryo Suspension is passed through a polyethylene tube (ca. 3 mm i.d.) and allowed to fall dropwise into a stirred, 50 mM $CaCl_2$ solution, with 2.1% M040 and 0.52% sucrose (final concentrations of M040 and sucrose are the same as in the sol). Each drop results in a synthetic seed.

(iii) Synthetic seeds are separated from the $CaCl_2$/M040/Sucrose solution, washed briefly with water to remove excess $CaCl_2$/M040/Sucrose, and combined with anhydrous drying agent to achieve a final water activity of about 97% RH. The mass of anhydrous drying agent required is calculated as outlined in the preceding process description. Approximately 0.75 g anhydrous silica gel per g of synthetic seed is required.

(iv) Dried synthetic seed is separated from the silica gel by sieving, and stored in an air tight (water impermeable) container at 20° C.

(v) Dried synthetic seed may be germinated by placing the seed on a medium (for example, agar-solidified GMD without sucrose) which supplies water and some of the nutrient requirements for germination.

A THIRD EMBODIMENT OF THE PROCEDURE DEVELOPED THROUGH EXPERIMENTATION:

Materials:
Propagule=spruce zygotic embryos removed from seed, and whole seed.
Filler=Natural silica ($SiO_2$; amorphous, finely ground, particle size 1–5 mm).
Binder=Sodium alginate (medium viscosity: 2% solution= ca. 3500 cp).
Dessicant=Silica gel (precipitated silica; silicic acid; approx. $H_2SiO_3$). 230–400 mesh particle size.
Other constituents=sucrose, maltodextrin/corn syrup solids $[(C_6H_{10}O_5)_n \cdot H_2O$; product of corn starch hydrolysis; e.g., Maltrin® M040 from Grain Processing Corp., Muscatine, Iowa, 52761, USA].
Processing:

(i) Zygotic embryos dissected from seed, or whole seed, are transferred to a sol composed of 1.0 g sodium alginate, 30.0 g silica, 1.4 g M040, 0.35 g sucrose, and 67.3 g water. Sixty somatic embryos per mL sol are used. This is the Propagule Suspension.

(ii) The Propagule Suspension is passed through a polyethylene tube (ca. 3 mm i.d.) and allowed to fall dropwise into a stirred, 50 mM $CaCl_2$ solution, with 2.1% M040 and 0.52% sucrose (final concentrations of M040 and sucrose are the same as in the sol). Each drop results in a synthetic seed.

(iii) Synthetic seeds are separated from the $CaCl_2$/M040/Sucrose solution, washed briefly with water to remove excess $CaCl_2$/M040/Sucrose, and germinated by placing the seed on a medium (for example, agar-solidified GMD) which supplies water and some of the nutrient requirements for germination.

Further Experimental Results:

1. Useful and Preferred Ranges of Binder and Filler in the Dispersion:

a) Binder.

Medium viscosity sodium alginate complexed with divalent calcium ion, is used at concentrations ranging from 0.25% to 3%, with the preferred concentration range being from 0.5% to 2.0% (percentages indicate the dry weight of alginate as a percent of the total mass of the Dispersion including filler).

b) Filler.

Natural silica (particle size distribution having approximately 80% by weight between 1 micron and 5 micron diameter) has a useful range between 10% to 50%, with the preferred range being 20% to 40% (percentages indicating the mass of silica as a percent of the total mass of the dispersion), and most preferably, about 30%.

Other filler materials that we have used to form the matrix include Indulin AT, (a trademark for a lignin product derived from wood pulp), α-cellulose, and starch.

2. Beads (subspherical, mean diameter ca. 2.1 mm when dry) of silica-alginate matrix were assessed at the Department of Agricultural and Bioresource Engineering, University of Saskatchewan, using a TA.XT2 Texture Analyzer (Stable Micro Systems). Beads were compressed at a rate of 0.8 mm/s. Dry beads required a mean of 20.81 Newtons (N)±0.77 N (±=SD; n=10) to cause fracture; fracture of the beads occurred at ca. 0.25 mm compression. When fully hydrated (1.5 h in water) the corresponding beads required less than 1N for 0.25 mm compression; compression up to 1.1 mm required only 7N and did not cause the beads to rupture.

These results confirm that the beads according to the invention have sufficent mechancial strength/hardness for use with mechanical seeding devices.

3. The matrix comprises 95 to 99%/w of silica, and 1 to 5%/w of alginate, based on the total weight of dry matter in the matrix. The preferred composition is 96.7%/w of silica and 3.3%/w of alginate.

It will be appreciated that, for other fillers, these percentages may change radically: for example, cellulose powder may be used as a filler, but because it has much lower density than silica, the same size bead is formed with a matrix composed of a very small mass of filler relative to the mass of alginate (note that the concentration of alginate in the Dispersion can be the same, but the resulting matrix has a much higher proportion of alginate on a mass basis).

We claim:

1. A synthetic seed comprising, a plant propagule capable of producing an entire plant, and an encapsulating material including a finely divided substantially biologically and chemically inert filler, a binder and water, wherein the encapsulating material is in the form of a matrix comprising silica in an amount of 95 to 99%/w, alginate in an amount of 1 to 5%/w, based upon the total dry weight of the matrix, and water, the synthetic seed having a water activity expressed as percent relative humidity and adjusted to a range that is compatible with the plant propagule, such that propagule viability is maintained and germination will occur when exposed to germination permissive conditions, and to provide sufficient mechanical strength/hardness for use with mechanical seeding devices.

2. A synthetic seed according to claim 1, wherein the binder is medium viscosity sodium alginate complexed with a divalent cation.

3. A synthetic seed according to claim 2, wherein the divalent cation is calcium, provided by calcium chloride.

4. A synthetic seed according to claim 2, wherein the filler is silica, having a particle size distribution of about 80 weight % between 1 and 5 microns in diameter.

5. A synthetic seed according to claim 4, wherein the silica is present in an amount of about 96.7%/w and the alginate is present in an amount of about 3.3%/w.

6. A synthetic seed according to claim 1, wherein the plant propagule is an embryo.

7. A synthetic seed according to claim 4, the matrix additionally comprising plant nutrients required for germination.

8. A synthetic seed according to claim 6, wherein the plant propagule is a whole seed or a zygotic embryo dissected from a whole seed.

9. A synthetic seed according to claim 4, the matrix additionally comprising sucrose in an amount of about 1.1% by weight based upon the dry weight of the matrix, and malto dextrin/corn syrup solids in an amount of about 4.3% by weight, based upon the dry weight of the matrix.

10. A synthetic seed according to claim 4, wherein the matrix binds about 4.5% of its own dry weight of water at 97% relative humidity.

11. A synthetic seed according to claim 1, wherein the water activity is adjusted to a range of 0 to 99% relative humidity.

* * * * *